(12) United States Patent
Seeber et al.

(10) Patent No.: US 7,397,902 B2
(45) Date of Patent: Jul. 8, 2008

(54) LEAF, MULTI-LEAF COLLIMATOR, DEVICE FOR DELIMITING BEAMS AND IRRADIATION DEVICE

(75) Inventors: Steffen Seeber, Heidelberg (DE); Joerg Stein, Heidelberg (DE); Stefan Goelz, Plankstadt (DE); John Juschka, Eberbach (DE); Martin Kolb, Bruehl (DE)

(73) Assignee: Siemens Aktiengesellschaft, Munich (DE)

( * ) Notice: Subject to any disclaimer, the term of this patent is extended or adjusted under 35 U.S.C. 154(b) by 397 days.

(21) Appl. No.: 10/507,508

(22) PCT Filed: Mar. 11, 2003

(86) PCT No.: PCT/EP03/02498

§ 371 (c)(1),
(2), (4) Date: Aug. 19, 2005

(87) PCT Pub. No.: WO03/079373

PCT Pub. Date: Sep. 25, 2003

(65) Prior Publication Data

US 2007/0127624 A1    Jun. 7, 2007

(30) Foreign Application Priority Data

Mar. 15, 2002    (DE) ................................ 102 11 492

(51) Int. Cl.
*G21K 1/04* (2006.01)
(52) U.S. Cl. ................ 378/152; 378/150; 250/505.1
(58) Field of Classification Search ................... 378/65, 378/147–153; 250/505.1
See application file for complete search history.

(56) References Cited

U.S. PATENT DOCUMENTS

| 3,448,270 | A | | 6/1969 | Peyser |
| 3,610,734 | A | | 10/1971 | Wollnik et al. |
| 4,794,629 | A | | 12/1988 | Pastyr et al. |
| 5,012,506 | A | * | 4/1991 | Span et al. ................. 378/152 |
| 5,889,834 | A | | 3/1999 | Vilsmeier et al. |
| 6,335,961 | B1 | | 1/2002 | Wofford et al. |
| 6,730,924 | B1 | | 5/2004 | Pastyr et al. |
| 2001/0043669 | A1 | | 11/2001 | Ein-Gal |

FOREIGN PATENT DOCUMENTS

| DE | 199 05 823 | 6/2000 |
| EP | 0 193 509 | 9/1986 |
| EP | 0 251 407 | 1/1988 |

* cited by examiner

Primary Examiner—Jurie Yun
(74) Attorney, Agent, or Firm—Paul Vincent

(57) ABSTRACT

The invention relates to a leaf (1) for a multi-leaf collimator (2) for delimiting a high-energy beam (3, 3', 3") of an irradiation device, in particular for conformational radiation therapy. According to the invention, the multi-leaf collimator (2) comprises a plurality of opposing leaves (1), which can be brought into the beam path (3, 3', 3") by means of drives (4), in such a way that the contour (5) of said path can be shaped in accordance with the volume to be irradiated. The need for beam-absorbent material (7) is reduced, as the leaf (1) essentially only comprises a beam-absorbent material (7) of an appropriate thickness (8) in a region (6) that is brought into the path (3, 3', 3") of the high-energy beam (3) during the course of all possible positional displacements (9). The invention also relates to a corresponding multi-leaf collimator (2), a device (22) for delimiting beams, and an irradiation device.

25 Claims, 3 Drawing Sheets

LEAF, MULTI-LEAF COLLIMATOR, DEVICE FOR DELIMITING BEAMS AND IRRADIATION DEVICE

This application is the national stage of PCT/EP03/02498 filed on Mar. 11, 2003 and Claims Paris Convention priority of DE 102 11 492.7 filed Mar. 15, 2002.

BACKGROUND OF THE INVENTION

The invention concerns a leaf for a multi-leaf collimator for delimiting a high-energy beam from an irradiation device, in particular, for conformation irradiation, wherein the multi-leaf collimator comprises a plurality of mutually opposite leaves which can be moved into the beam path via drives, such that the contour of the beam path can be shaped in accordance with the volume to be irradiated.

The invention also concerns a multi-leaf collimator for delimiting a high-energy beam from an irradiation device, in particular, for conformation irradiation, comprising a plurality of mutually opposite leaves which can be moved into the beam path via drives, such that the contour of the beam path can be shaped in accordance with the volume to be irradiated.

The invention also concerns a device for delimiting a high-energy beam from an irradiation device, in particular, for conformation irradiation, comprising a multi-leaf collimator having a plurality of mutually opposite leaves which can be moved into the beam path via drives, such that the contour of the beam can be shaped in accordance with the volume to be irradiated, and with a further shielding for delimiting the path of the high-energy beam.

The invention furthermore concerns an irradiation device, in particular for stereotactic conformation irradiation, with means for delimiting a high-energy beam from the irradiation device using a multi-leaf collimator comprising a plurality of mutually opposite leaves which can be moved into the beam path via drives, such that the contour of the beam can be shaped in accordance with the volume to be irradiated, and with means for delimiting the path of the high-energy beam using further shielding.

A leaf, a multi-leaf collimator, a device for beam delimitation and an irradiation device of this type are known in the art, e.g. from EP 0 193 509 A2.

All beam-absorbing materials, large amounts of which are required for the above-mentioned tasks, have a very large specific weight which complicates handling of the collimators on the irradiation devices, in particular, exchange thereof. A further problem is that tungsten, which is advantageous as a radiation-absorbing material and is therefore most frequently used, is expensive and the price and delivery times are also subject to very large, politically dependent, variations on the world market, since tungsten is also used for the production of weapons.

It is therefore the underlying purpose of the invention to reduce the need for radiation-absorbing material to as great an extent as possible.

SUMMARY OF THE INVENTION

This object is achieved in accordance with the invention with respect to the leaf, in that the leaf comprises radiation-absorbing material of appropriate thickness only in that region which can project into the path of the high-energy beam in all possible adjustment positions. The object for the multi-leaf collimator is achieved in a corresponding manner.

This object is achieved with respect to the device for beam delimitation and irradiation devices, in that the leaves comprise a radiation-absorbing material of appropriate thickness substantially only in that region which can project into the path of the high-energy beam and which is not shielded by the further shielding in all possible adjustment positions.

The invention considerably reduces the need for radiation-absorbing material for the above-mentioned items without thereby considerably reducing the shielding effect. This considerably reduces the weight and facilitates handling. In particular, exchange of collimators on the irradiation devices is facilitated since the enormous weight thereof can be considerably reduced.

Further advantages are reduction in cost for the above-mentioned items and storage, in particular, of tungsten which needs to be stored due to the fact that its availability cannot always be guaranteed.

In a suitable design of the leaf, the other region which does not absorb radiation substantially consists of another material having a lower specific weight than the beam-absorbing material and having good mechanical properties. The beam-absorbing material is preferably tungsten and the material in the region which does not absorb radiation is preferably steel. This is advantageous since the weight of steel is only approximately half the weight of tungsten and the weight of the leaf is therefore considerably reduced. The use of steel is moreover advantageous in that there is a wide range of different steel types from which the most favorable properties can be selected. In particular, the surface of the steel may be improved or hardened to thereby adjust breaking strength and elasticity as well as provide excellent wear resistance.

The beam-absorbing material is preferably joined with the other material such that, in the front position of the leaf, the other material is still slightly outside of the outermost delimitation of the high-energy beam. Substantially only that region which must be absorptive for the high-energy beam is produced from the beam-absorbing material and not the other region. The beam-absorbing region only has a slight margin of safety. An inclination of the joint in correspondence with the outermost possible delimitation of the high-energy beam produces optimum reduction in beam-absorbing material.

In a further design, the beam-absorbing material is joined to the other material at an angle. Although this does not produce the above-mentioned optimum result, the angular shape of the joint can lead to a higher stability. Another possibility to achieve such stability is to insert the beam-absorbing material into a recess of the further material, such that the beam-absorbing material is surrounded on three sides by the further material. The further material thereby comprises two holding bars on the upper and lower sides of the beam-absorbing material.

In a highly suitable construction of a leaf, the leaf consists of a rear part of the other material and a front part of the beam-absorbing material, wherein two narrow elongated parts are joined at the top and bottom which are designed as a guiding part and a driving part. The guiding part may e.g. comprise a guiding groove and the driving part may comprise a toothed rack for engagement of the toothed wheel of the leaf drive. The above-mentioned narrow, elongated parts are preferably produced from the other material, e.g. steel. To reduce production costs, these parts may be prefabricated, profiled material.

The material of the leaves may e.g. be joined by soldering. To reduce production costs, joining is effected by producing a wide block which has the design of the leaves but a multiple width thereof. The leaves may then be separated from this block, e.g. through sawing, spark erosion, laser cutting or in another manner.

The leaf materials may be glued to each other. It is also possible to join two narrow parts to the rear and front parts using tongue and groove joints. The joint may be provided through pressing, additional adhesive, or soldering.

The weight is further reduced when the region of the leaf which does not enter into the beam path has openings. These may also be provided in the above-mentioned block, such that each leaf already has these openings after separation of the leaves from this block, thereby reducing the production costs.

The inventive multi-leaf collimator can also be designed such that its leaves have any combination of the above-mentioned features. Since the multi-leaf collimator has a plurality of such leaves, its weight is also considerably reduced and mounting or removing such a multi-leaf collimator to or from an irradiation device is substantially facilitated.

In one design of the inventive device for delimiting a cluster of high-energy beams of an irradiation device, the further shielding is disposed before the multi-leaf collimator, relative to the beam path. In an alternative embodiment, the further shielding is disposed behind the multi-leaf collimator, relative to the beam path. This is not important for the overall shielding result, rather merely guarantees that no portion of the beam circumvents the delimited shielding region of the multi-leaf collimator due to insufficient shielding.

The further shielding may be a fixed frame or a shielding collimator whose opening region can be adjusted. A shielding collimator of this type can comprise e.g. two radiation delimiting elements which can be brought into different positions. Beam-absorbing material and therefore weight can also be reduced with such a shielding collimator when these radiation delimiting elements have beam-absorbing material of corresponding thickness only in that region which can enter into the beam path of the high-energy beam at all adjustment positions.

The inventive dimensions of the regions of the leaves which consist of beam-absorbing and other materials, depend on the path of the high-energy beam to be delimited. Since the shielding collimator delimits the contour of this high-energy beam, which must then be further delimited by the multi-leaf collimator, the delimitation of the beam path by the shielding collimator is important for dimensioning these regions of the leaves. The beam geometry with respect to delimitation and also the distance between the shielding collimator and the multi-leaf collimator are thereby decisive.

These relations which are to be taken into consideration permit different designs. The dimensions of the leaf regions may e.g. be determined by their mechanically maximum possible adjustment motions. Moreover, the dimensions of the leaf regions can be determined by the mechanically maximum opening of the shielding collimator. Through combination of these two possibilities, the respectively maximum mechanically defined openings form the basis for dimensioning of the leaf regions.

In another possibility which permits a wider variety of combinations of shielding collimators and multi-leaf collimators, the mechanically maximum possible opening is replaced by a delimitation which is realized through control technology. The dimensions of the leaf regions can be determined using possible adjustment motions which are delimited through control technology and, with respect to the shielding collimator, using adjustment motions of the shielding collimator which are also delimited through control technology.

The inventive device can, of course, be constructed with multi-leaf collimators and leaves which include any combination of the above-mentioned further developments and designs. The same applies to an irradiation device of the inventive type which may, of course, also comprise all designs of the above-mentioned device for delimiting a high-energy beam.

BRIEF DESCRIPTION OF THE DRAWING

The invention is explained below with reference to embodiments shown in the drawing.

DESCRIPTION OF THE PREFERRED EMBODIMENT

Figure 1:
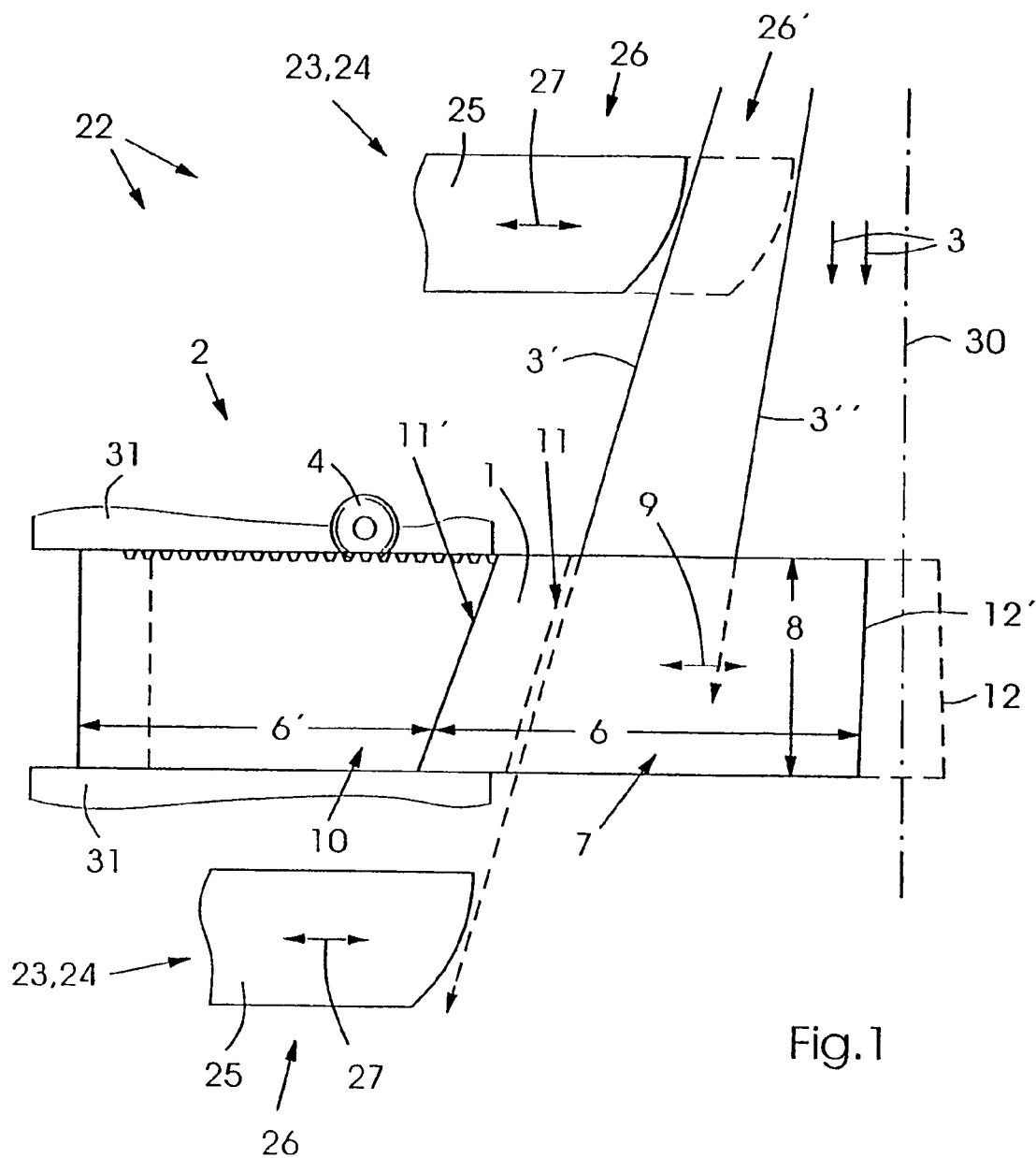
FIG. 1 shows a design of a device for delimiting a cluster of high-energy beams.

FIG. 1 shows a design of a device 22 for delimiting a cluster of high-energy beams 3. This device 22 consists of a multi-leaf collimator 2 and a further shielding 23. This further shielding 23 can be disposed above or alternatively below the multi-leaf collimator 2. The design of the device 22 generally includes one of these alternatives, which are both shown in FIG. 1 for reasons of simplicity, and does not exclude use of two shieldings 23. Moreover, only the left-hand half of the device 22 is shown. The right-hand half, which is mirror-symmetrical to the central line 30, is not shown.

Figure 2:
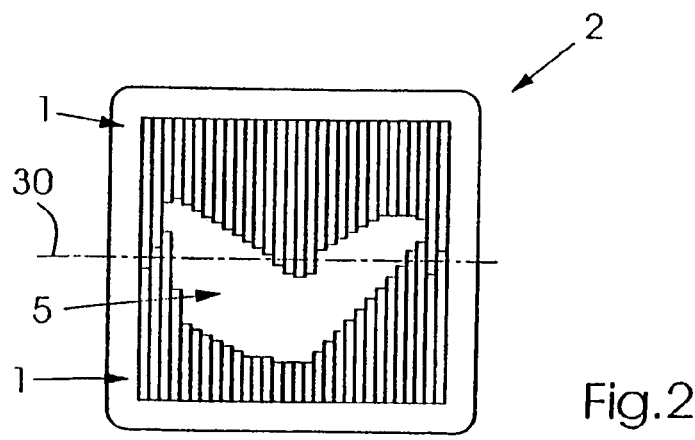
FIG. 2 shows a schematic sketch of a multi-leaf collimator.

The design of the leaf 1 is essential to the invention. The multi-leaf collimator 2 comprises a large number of such leaves on both sides of the central line 30 as is shown in FIG. 2 in the form of a schematic sketch thereof.

In this design, the leaf 1 comprises two regions 6 and 6' one of which 6 can enter into the path 3, 3', 3" of the high-energy beam 3, and consists of beam-absorbing material 7, and another region 6' which does not enter into the beam path 3, 3', 3" and which consists of another material 10, e.g. steel.

The various positions 12, 12' of the front edge of a leaf 1 are obtained by disposing it in guides 31 to be displaceable in the direction of the adjustment motion 9 and moved into the various positions using a drive 4. It must thereby be ensured that in any of these positions between 12 and 12', i.e. also in the front position 12, it is guaranteed that the outermost delimitation 3' of the high-energy beams 3 impinge on the beam-absorbing material 7, thereby defining the dimensions of the regions 6 and 6' of the leaf 1, wherein the rearmost position of joining of the regions 6, 6' is designated with 11' and the front position is designated with reference numeral 11. The full thickness 8 of the beam-absorbing material 7 is thereby always active.

It is also, of course, possible to exert an adjustment motion 27 on the shielding collimator 24, irrespective of whether it is disposed above or below the multi-leaf collimator 2. It can thereby assume a position 26, 26' or another position which permits resetting of the delimitation of the high-energy beams 3 e.g. to the beam edge 3". If such a delimitation 3" is safeguarded e.g. by corresponding technical control measures, the materials 7 and 10 of the leaves 1 could also be joined differently 11, 11' i.e. have regions 6, 6' of different subdivision. In this case, it must merely be ensured that this joint 11, 11' is always outside of the delimitation 3". In a corresponding manner, this result could, of course, also be obtained by corresponding delimitation of the adjustment motion 9 of the leaves 1.

FIG. 2 shows a diagrammatic sketch of a multi-leaf collimator 2, wherein the leaves 1 are shown on both sides of the central line 30. Appropriate adjustment motions 9 of the leaves 1 can shape the contour 5 of the high-energy beam 3 to correspond to the volume to be irradiated, thereby taking into consideration the divergent beam path 3, 3', 3".

Figure 3:
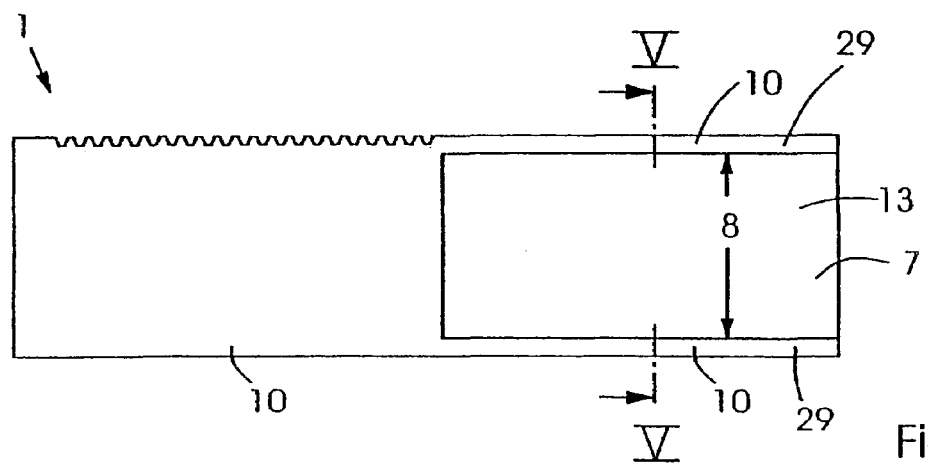
FIG. 3 shows a first embodiment of a leaf.
Figure 5:
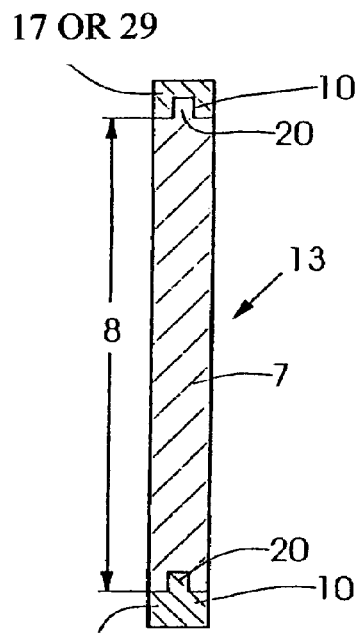
FIG. 5 shows a section V-V through FIG. 3 or FIG. 4.

FIG. 3 shows a first embodiment of a leaf 1. The design provides that the other material 10 has two holding bars 29 towards the front, which form a recess 13 in which the radiation-absorbing material 7 is inserted. It must, of course, have the full thickness 8 which is required for absorption of the beams 3. This increases the stability and provides good seating of the beam-absorbing material 7. FIG. 5 shows a sectional view V-V.

Figure 4:
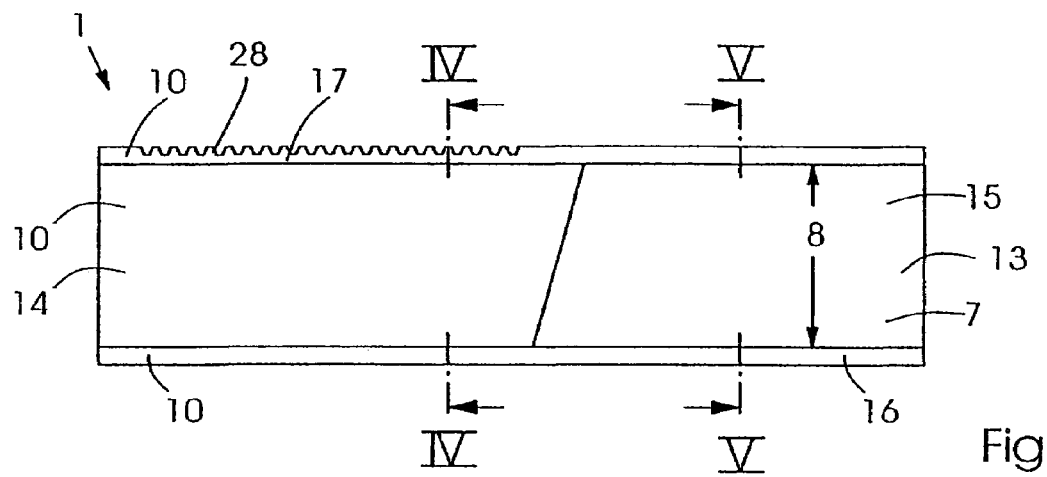
FIG. 4 shows a second embodiment of a leaf.

FIG. 4 shows a second embodiment of a leaf 1. It consists of a rear part 14 and a front part 15, wherein the rear part 14 consists of the other material 10, e.g. steel, and the front part 15 consists of the beam-absorbing material 7, e.g. of tungsten. These two parts 14 and 15 are located between two narrow, elongated parts 16 and 17, wherein 16 is a guiding part and 17 is a driving part. The driving part 17 may e.g. be a toothed rack 28 and the guiding part 16 a guide 31 comprising guiding groove 32 which runs in a rail of complementary design. The latter is shown in FIG. 6, as is the design of the driving part 17 as a toothed rack 28.

FIG. 5 shows a section V-V which may be identical to FIG. 3 and FIG. 4. The upper and lower sides of the beam-absorbing material 7 may be provided with a guiding part 16 and a driving part 17 or with one holding bar 29 each. For secure and accurate connection, a tongue and groove joint 20 may be provided while ensuring that the thickness 8 of the beam-absorbing material 7 is maintained over the entire width 8.

Figure 6:
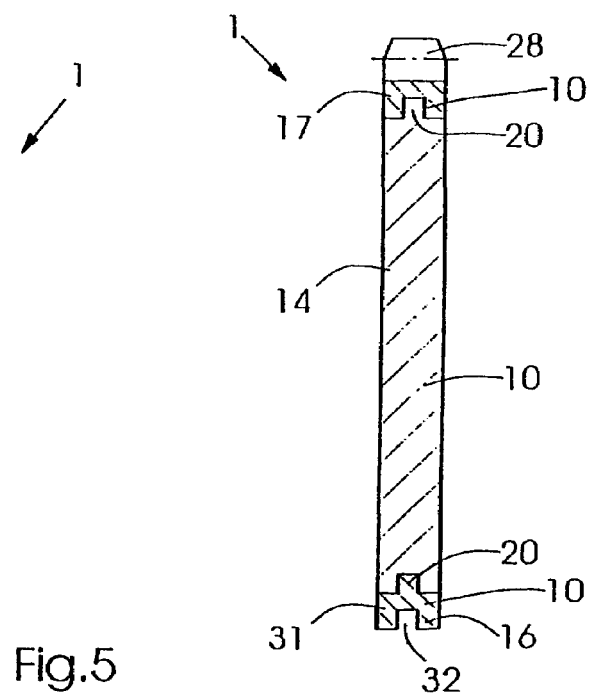
FIG. 6 shows a section through FIG. 4.

FIG. 6 shows a section VI-VI through FIG. 4 in the region of the toothed rack 28 and in the rear region of the guiding part 16 where it comprises the guiding groove 32 which runs in a corresponding rail. Good connection may also be provided through tongue and groove joints 20.

Figure 7:
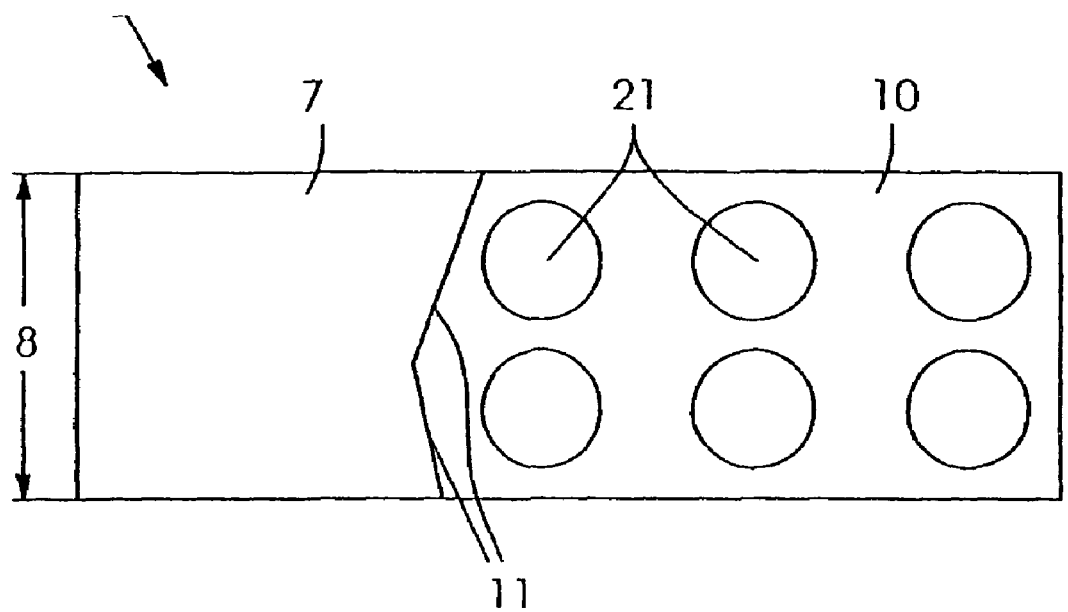
FIG. 7 shows a third embodiment of a leaf.

FIG. 7 shows a third embodiment of a leaf 1 which comprises a joint 11 of angular design to increase stability and provide exact seating. The region of the leaf 1 which consists of the other material 10, e.g. steel has openings 21 to further reduce weight. FIG. 7 may also represent a block 18 since it is designed in an identical manner to the leaves 1, but has multiple times the width 19 such that the individual leaves 1 can be cut therefrom.

Figure 8:
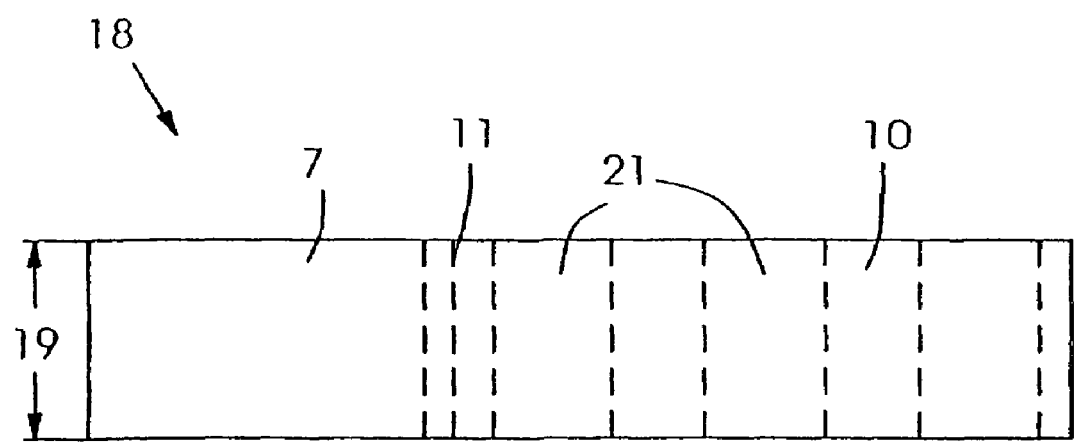
FIG. 8 shows a block from which the leaves can be separated.

FIG. 8 shows such a block, wherein identical reference numerals represent the above-mentioned parts. It shows that all above-mentioned designs may already be provided such that the leaves 1 shown in FIG. 7 can be produced after cutting the block 18.

The drawing shows, of course, only a selection of possible features of the inventive items. They can be combined in any arbitrary manner. Each inventive leaf 1 may e.g. comprise recesses 21. The leaves 1 may also be designed in another manner, e.g. have front edge adjustment or another design for joining of the individual parts of the leaf 1.

Leaf, Multi-leaf Collimator, Device for Delimiting Beams and Irradiation Device

LIST OF REFERENCE NUMERALS 1 leaf
2 multi-leaf collimator
3,3',3" beam path of a high-energy beam
3 high-energy beam
3' outermost delimitation of the high-energy beam through shielding
3" delimitations of the high-energy beam through an adjustment position of a shielding collimator
4 leaf drives
5 contour of the high-energy beam, shaped by the multi-leaf collimator
6,6' leaf regions
6 region which can enter into the beam path of the high-energy beam and
6' region which cannot enter into this beam path
7 beam-absorbing material
8 thickness of the beam-absorbing material
9 adjustment motions of the leaf
10 other material (of the region which cannot enter into the beam path)
11,11' joining of the materials 7 and 10
11 front position of joining
11' rear position of joining
12,12' leaf positions (of the leaf front edge)
12 front position
12' rear position
13 recess
14 rear part
15 front part
16 guiding part
17 driving part
18 block
19 width of the block
20 tongue and groove joints
21 openings
22 device for delimiting a high-energy beam
23 further shielding
24 shielding collimator
25 beam delimiting elements of the shielding collimator
26, 26' positions of the beam delimiting elements
26 mechanically maximum opening
26 ' set opening
27 adjustment motion of the shielding collimator
28 toothed rack
29 holding bars
30 central line of the device 22 or of the multi-leaf collimator
31 leaf guide
32 guiding groove

We claim:

1. A leaf for a multi-leaf collimator to delimit a high-energy beam of an irradiation device, for conformation irradiation, wherein the multi-leaf collimator comprises a plurality of mutually opposite leaves which can be brought into a beam path via drives such that a contour of the beam path can be shaped in accordance with a volume to be irradiated, the leaf comprising:

a beam-absorbing material of appropriate thickness and disposed substantially only in a region which can enter into the path of the high-energy beam in all possible adjustment positions of the leaf, wherein the leaf comprises an other region which does not absorb the beam, said other region consisting essentially of an other material having lower atomic number than said beam-absorbing material and also having good mechanical properties.

2. The leaf of claim 1, wherein said beam-absorbing material is tungsten.

3. The leaf of claim 1, wherein said other material is steel.

4. The leaf of claim 1, wherein said beam-absorbing material is joined to said other material such that, in a front position of the leaf, said other material is still slightly outside of an outermost possible delimitation of the high-energy beam.

5. The leaf of claim 1, wherein said beam-absorbing material is joined to said other material, thereby forming angles.

6. The leaf of claim 1, wherein said beam-absorbing material is introduced into a recess in said other material such that said beam-absorbing material is surrounded by said other material at three sides.

7. The leaf of claim 6, wherein the leaf consists essentially of a rear part of said other material and a front part of said beam-absorbing material and further comprising a first narrow elongated part joined at a top of the leaf and a second narrow elongated part joined at a bottom of the leaf, wherein said first and said second parts constitute a guiding part and a driving part.

8. The leaf of claim 7, wherein said first and said second narrow elongated parts consist essentially of said other material.

9. The leaf of claim 7, wherein said first and second narrow parts are joined to said front and rear parts through tongue and groove joints.

10. The leaf of claim 1, wherein said beam-absorbing material and said other material are soldered together.

11. The leaf of claim 10, wherein the leaf is produced through separation from a block which is designed like the leaf, but has a multiple width thereof.

12. The leaf of claim 1, wherein said beam-absorbing material and said other material are glued together.

13. The leaf of claim 1, wherein said other material has openings.

14. A multi-leaf collimator for delimiting a high-energy beam of an irradiation device for conformation irradiation, the collimator comprising:
a plurality of mutually opposite leaves which can be brought into a beam path via drives such that a beam contour can be shaped in accordance with a volume to be irradiated, wherein each of said leaves comprises a beam-absorbing material of appropriate thickness only in a region which may enter into a path of the high-energy beam for all possible adjustment positions of the collimator, wherein the leaf comprises an other region which does not absorb the beam, said other region consisting essentially of an other material having a lower atomic number than said beam-absorbing material and also having good mechanical properties.

15. A device for delimiting a high-energy beam for conformation irradiation, the device comprising:
a multi-leaf collimator having a plurality of mutually opposite leaves which can be brought into a beam path via drives, such that a contour of the beam can be shaped in accordance with a volume to be irradiated; and
a further shielding to delimit a path of the high-energy beam, wherein said leaves each comprise a beam-absorbing material of appropriate thickness only in a region which can enter into the path of the high-energy beam and which is not shielded by said further shielding at all possible adjustment positions of said leaves, wherein each of said leaves comprises an other region which does not absorb the beam, said other region consisting essentially of an other material having a lower atomic number than said beam-absorbing material and also having good mechanical properties.

16. The device of claim 15, wherein said further shielding is disposed in front of said multi-leaf collimator.

17. The device of claim 15, wherein said further shielding is disposed behind said multi-leaf collimator.

18. The device of claim 15, wherein said further shielding is a shielding collimator having an adjustable opening.

19. The device of claim 18, wherein said shielding collimator comprises two radiation delimiting elements which can be brought into different positions.

20. The device of claim 19, wherein said radiation delimiting elements comprise beam-absorbing material of corresponding thickness only in a region which can enter into a path of the high-energy beam collimator at all possible adjustment positions of said shielding collimator.

21. The device of claim 18, wherein dimensions of regions of said leaves are determined by a maximum mechanical opening of said shielding collimator.

22. The device of claim 18, wherein dimensions of regions of said leaves are determined by adjustment motions of said shielding collimator as delimited through control technology.

23. The device of claim 15, wherein dimensions of regions of said leaves are determined by maximum possible mechanical adjustment motions thereof.

24. The device of claim 15, wherein dimensions of regions of said leaves are determined on a basis of a possible adjustment motions of said leaves as delimited by control technology.

25. An irradiation device for conformation irradiation, the device comprising:
means for delimiting a high-energy beam emitted by an irradiation source, said delimiting means having a multi-leaf collimator comprising a plurality of mutually opposite leaves which can be brought into a beam path via drives such that a contour of the beam path can be shaped in accordance with a volume to be irradiated, said delimiting means also comprising a further shielding for delimiting a path of the high-energy beam, wherein each of said leaves comprises a beam-absorbing material of appropriate thickness only in a region which can enter into a path of the high-energy beam and which is not shielded by said further shielding for all possible adjustment positions, wherein each of said leaves comprises an other region which does not absorb the beam, said other region consisting essentially of an other material having a lower atomic number than said beam-absorbing material and also having good mechanical properties.

* * * * *